Figure 1:
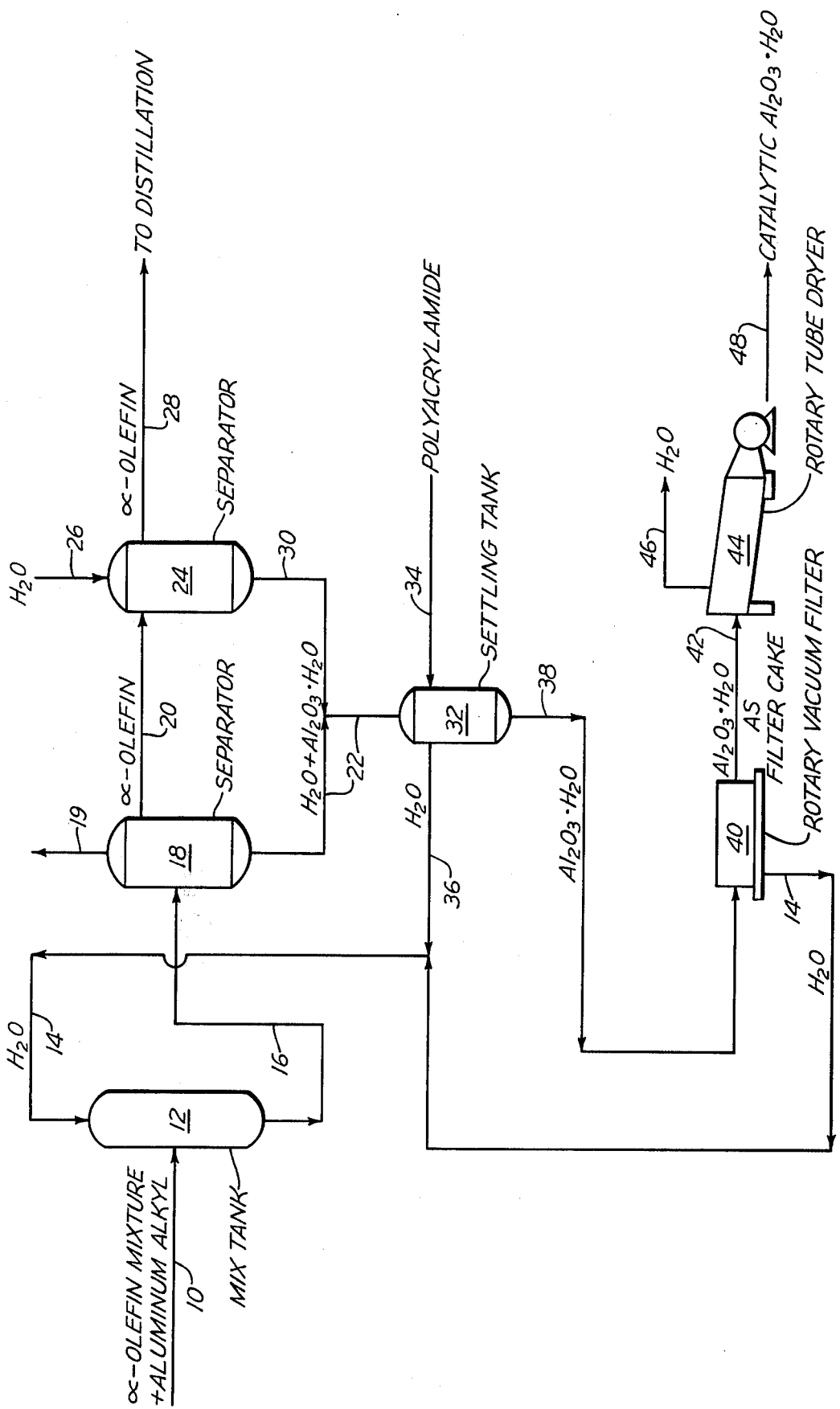

United States Patent [19]

Beuther et al.

[11] 4,022,839

[45] May 10, 1977

[54] RECOVERY OF ALUMINUM FROM ETHYLENE TELOMER PRODUCT

[75] Inventors: Harold Beuther, Gibsonia; William L. Kehl, Indiana Township, Allegheny County; Harold E. Swift, Gibsonia, all of Pa.

[73] Assignee: Gulf Research & Development Company, Pittsburgh, Pa.

[22] Filed: June 25, 1976

[21] Appl. No.: 699,899

[52] U.S. Cl. .................. 260/677 A; 260/683.15 R
[51] Int. Cl.$^2$ ...................................... C07C 11/02
[58] Field of Search ............... 260/677 A, 683.15 R

[56] References Cited

UNITED STATES PATENTS

| 3,637,885 | 1/1972 | McClaflin | 260/677 A |
| 3,696,161 | 10/1972 | Kobetz et al. | 260/677 A |

Primary Examiner—C. Davis

[57] ABSTRACT

When ethylene is telomerized to produce alpha-olefins in the presence of an organo-aluminum catalyst, the aluminum catalyst is present in the normally liquid alpha-olefin product and must be removed prior to distillation of that product. This removal is accomplished in two zones. Water is added to the alpha-olefin product containing the organo-aluminum catalyst in a first zone to produce an aqueous phase containing a suspension of aluminum hydroxide and an organic phase containing the alpha-olefins. After removal of the organic phase, a sufficient amount of an aqueous solution of a polyacrylamide in anionic form is added to the aqueous phase to result in at least 90 percent of the aluminum hydroxide settling in a time period of less than ten minutes at ambient conditions.

8 Claims, 2 Drawing Figures

Fig. 1
RECOVERY OF ALUMINUM FROM ETHYLENE TELOMER PRODUCT

RECOVERY OF ALUMINUM FROM ETHYLENE TELOMER PRODUCT

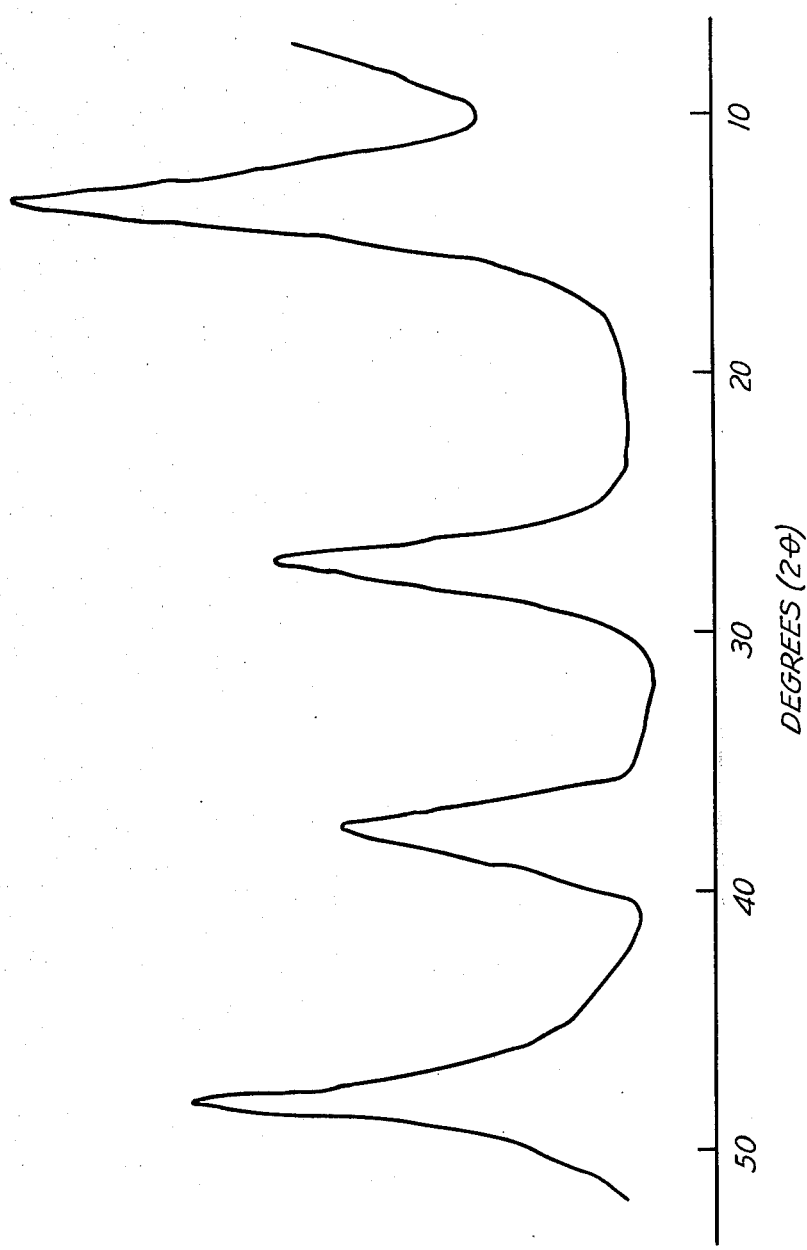

RECOVERY OF ALUMINUM FROM ETHYLENE TELOMER PRODUCT

This invention relates to the removal of aluminum values from the reaction product of an ethylene telomerization reaction.

BACKGROUND OF THE INVENTION

There are many techniques described in the prior art for the preparation of alumina. Apparently, however, the source of aluminum values and/or the technique of treatment, such as drying, results in different forms of alumina which possess different physical and catalytic properties. Many of the aluminas, for example, are used as supports for various types of catalysts used in the petroleum and other industries. For example, it is known that aluminas derived from a byproduct of the Ziegler alcohol synthesis reaction are particularly pure and are therefore useful as a support for reforming catalysts (U.S. Pat. No. 3,852,190 to Buss et al.). Buss et al. confirm or at least suggest that a variety of aluminas can be made, and the most frequently preferred alumina for use in reforming catalysts is gamma-alumina (see Col. 2, lines 41–42 of the Buss et al. patent). W. B. Carter in U.S. Pat. No. 3,264,063 teaches the preparation of eta-alumina from aluminum alcoholates by introducing the aluminum alcoholates to the surface of a body of water, e.g. by spraying. On the other hand, R. L. Poe in U.S. Pat. No. 3,309,416 teaches the preparation of beta-alumina from the hydrolysis of aluminum trialkoxide. Poe also teaches in Column 4, lines 18 et seq., that the alumina hydrate produced by the hydrolysis of the aluminum trialkoxides is "yielded through line 31". Line 31 refers to the Figure in the Poe et al. reference, but no technique is taught for the recovery of the alumina hydrate from the material removed through Poe's line 31, and no teachings are present indicating any special problems associated with the alumina hydrate. J. J. Hagan et al. in U.S. Pat. No. 3,751,518 are also concerned, like Poe, with olefin production via a growth-displacement reaction in the presence of organo-metallic catalysts, and teach in Column 7 that the catalyst in the product may be deactivated by contact with acid, base, water, or alcohol, but dilute caustic is preferred. This generally follows the earlier teachings of H. B. Fernald et al. in U.S. Pat. No. 3,482,000, but more especially in Fernald et al.'s U.S. Pat. No. 3,477,813. In the '813 patent in Column 5, Fernald et al. teach away from the use of plain water for the conversion of the aluminum alkyls to hydrated oxides, as the plain water tends to cause the hydrated aluminum oxides to precipitate upon the walls of said zone and in transfer lines and instrument lines, etc. Because of this problem, Fernald et al teach it is preferred to maintain the aluminum in solution in a first aluminum-removal zone by reaction with caustic so as to avoid the precipitation problems in the transfer line, etc. In Column 2, lines 38 et seq., Fernald et al. caution that if too much caustic is added, the excessive water introduced prevents rapid settling of alumina oxides later in the process.

It appears obvious that the reason why Fernald et al. were having problems with precipitation in the transfer lines, etc., was because of the slow rate at which the hydrated aluminum oxides tended to settle out from the aqueous product solution. This has been found to be true in the experimental work to be discussed below, but it has also been found in accordance with the present invention that the addition of small amounts of a particularly defined anionic form of polyacrylamide tend to result in a rapid settling of substantially all of the finely dispersed colloidal size hydrated alumina oxide particles from the ethylene growth-displacement product using an aluminum alkyl type catalyst when such reaction product is contacted with plain water.

In accordance with the invention, the aluminum values are rapidly and substantially completely removed from the product stream of an alpha-olefin process wherein ethylene is telomerized to alpha-olefins in the presence of an organo-aluminum catalyst to produce the product stream containing said organo-aluminum catalyst in the alpha-olefins. The process of this invention comprises mixing water with said product stream in an amount sufficient to produce (1) an aqueous phase containing a fine colloidal suspension of hydrated aluminum oxide particles and (2) an organic alpha-olefin phase substantially free of aluminum values. The aqueous and organic phases are suitably separated, and to the aqueous phase is added a sufficient amount of an aqueous solution of a polyacrylamide to result in at least 90 weight percent of the hydrated aluminum oxide settling in less than 10 minutes at ambient conditions. The polyacrylamide has the formula:

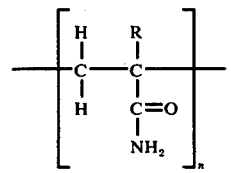

where R can be hydrogen or a hydrocarbon group having from 1 to 6 carbon atoms; $n$ is from $80 \times 10^3$ to $15 \times 10^5$; and wherein a sufficient portion of the $NH_2$ groups are coverted to an acid salt form to impart anionic properties to the polyacrylamide. Preferably two aluminum removal zones are employed in a continuous process as will be described below.

Ethylene is telomerized to normal alpha-olefins having between about 4 and 40 carbon atoms in the presence of an organo-aluminum catalyst, such as triethyl aluminum, which is charged to the process in a catalyst solvent. The reaction temperature can be between about 180° and 240° C.; the reaction pressure is at least about 1000 pounds per square inch; there is between about $1 \times 10^{-4}$ and $1 \times 10^{-2}$ moles of catalyst per mole of ethylene, and the polymerization proceeds until there is a conversion of about 30 to 60 percent of said ethylene to polymer product. These process conditions are illustrative only and are not per se a part of the present invention. Further details of a suitable process for producing alpha-olefins can be found in U.S. Pat. No. 3,482,000 issued Dec. 2, 1969, the teachings of which are incorporated herein by reference.

In general, the product from the alpha-olefin process, disregarding catalyst solvent, comprises between about 10 and 75 weight percent unreacted ethylene, the remainder being alpha-olefin product, and between about 0.2 to about 4 weight percent of organo-aluminum catalyst having three alkyl groups with each group having an average of about 8 carbon atoms. For example, the product from the alpha-olefin process commonly comprises about 48 to 50 weight percent unreacted ethylene, about 48 to 50 weight percent alpha-olefin product and about 2 weight percent of organo-aluminum catalyst. The product from the alpha-olefin process is generally at a pressure between about 1500 and 4000 pounds per square inch or higher. It is important to substantially completely remove all the aluminum prior to charging the alpha-olefin product to a distillation column for the fractionation thereof. The presence of aluminum under distillation conditions will seriously degrade the alpha-olefin product and be generally deleterious to the distillation operation. This invention relates to a highly advantageous method for the removal of the aluminum from the product prior to charging said product to a distillation zone.

In accordance with this invention, the aluminum is removed from alpha-olefin product in a continuous process employing two aluminum-separation zones. Just prior to the first aluminum-separation zone, some ethylene gas is vented from the alpha-olefin reactor upwardly to reduce the pressure to between 50 and 1000 psig; and a mixture comprising unreacted ethylene, alpha-olefin product, catalyst solvent and organo-aluminum catalyst is admixed with the desired amount of water in a mixing tank.

In the first aluminum-separation zone, separate organic and aqueous layers form. The aqueous layer comprises a colloidal suspension of alumina particles. (The terms "alumina", "hydrated aluminum oxide" and "aluminum hydroxide" are used interchangeably in this application.) Gaseous ethylene is vented from the first zone so that the organic layer comprises the liquid alpha-olefin product together with some emulsified water.

If too little water is used, complete removal of aluminum is difficult. If too much water is used, unnecessarily large volumes must be handled which would needlessly increase the expense of the operation. Thus the amount of water should be sufficient to result in the production of an aqueous phase containing a fine colloidal suspension of hydrated aluminum oxide particles and an organic phase containing the alpha-olefin and being substantially free of aluminum values.

The volume ratio of water to the alpha-olefin reaction product can suitably be from 0.25:1 to 2:1, preferably 0.5:1 to 1:1.

The contacting is done at temperature conditions which do not result in vaporization of the higher alpha-olefin products, or, of course, the water. The temperature must be high enough, however, to maintain the alpha-olefin product in the liquid phase since the alpha-olefin product does tend to solidify to a wax-like mass on cooling to room temperature. Normally, temperatures of 40° to 85° C, preferably 50° to 75° C., are employed.

The aqueous colloidal suspension of alumina is generally and conveniently removed to a second aluminum-separation zone in order to maintain a continuous form of operation. If the colloidal suspension of alumina were allowed to settle of its own accord, inordinate and unacceptable amounts of time would be required from a commercial standpoint in order to result in substantially complete settling of the alumina to a filterable form.

As noted earlier, Fernald et al. in Column 2, lines 36 to 38 of U.S. Pat. No. 3,477,813, teach that excessive water introduced with their caustic will prevent rapid settling of aluminum hydroxide in the process. Indeed times on the order of weeks might be required in order to obtain substantially complete settling of the aluminum hydroxide, if at all. There are a number of coagulant or precipitation aids on the market which might be useful in coagulating colloidal particles such as are present in the aqueous stream described above. There is no known way of predicting ahead of time whether or which of the coagulant aids which are available will function in any particular environment. A number of coagulant aids were tried with the aqueous product stream described above, but only an anionic form of a polyacrylamide to be described below was found not only to coagulate the colloidal aluminum particles but also to result in a rapid settling of the alumina particles. By a "rapid settling" is meant that over 90 percent of the colloidal alumina had settled out in a period of time of less than 10 minutes. The savings in caustic alone over the technique described by Fernald et al. and others in the prior art (in addition to avoiding the pollution problems associated with the use of caustic) constitute extra and added benefits to the process of this invention. In addition, as will be described below, extremely minute quantities of the polyacrylamide have been found sufficient to perform the coagulation of the colloidal alumina particles.

Thus, in accordance with the invention, it has been found that an aqueous solution of certain high molecular weight polyacrylamides in anionic form possess unexpectedly superior properties not only in coagulating the alumina from an ethylene-growth displacement reaction product containing an organo-aluminum catalyst, but also in substantially completely settling the alumina in periods of time of less than 10 minutes. The polyacrylamide has the general formula:

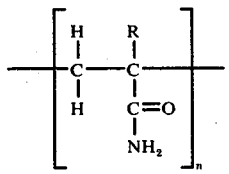

where R can be hydrogen or a hydrocarbon group having from 1 to 6 carbon atoms; $n$ is from $80 \times 10^3$ to $15 \times 10^5$; and wherein a sufficient portion of the $NH_2$ groups are converted to an acid salt form to impart anionic properties to the polyacrylamide.

The polyacrylamide suitably has a molecular weight of from one million to 100 million, which can be measured by light scattering, viscosity or osmotic techniques; and usually the molecular weight is from 6 million to 10 million.

The preparation of the polyacrylamides forms no part of this invention, for the preparation of these materials is well known to those having ordinarily skill in the art. For example, a suitable description of acrylamide polymers and their method of preparation can be found in the Encyclopedia of Polymer Science and Technology, Volume I, pages 177–195, published by Interscience Publishers, Div. of John Wiley & Sons, Inc., and other references contained therein.

The polyacrylamides which are useful as coagulating agents in the process of this invention have a sufficient portion of the $NH_2$ groups converted to an acid salt form so as to impart anionic properties to the polyacrylamide. Suitably from 5 to 25 mole percent of the $NH_2$ groups are converted. Preferably about 15 percent of the amine groups are converted to the acid salt form.

The conversion of the amine groups to an acid salt form can be achieved by techniques which are well known to those having ordinary skill in the art. For example, the polyacrylamide can be reacted with the desired amount of a strong inorganic acid such as sulfuric acid to form ammonium sulfate and to convert the desired amount of amide linkages to acid linkages. Polyacrylamides made in aqueous solution are likely to have undergone appreciable hydrolysis of amide groups to carboxyl groups. This hydrolysis can be enhanced by adding the corresponding amount of sodium hydroxide (or other basic hydroxides) during polymerization. The resultant polymer thus contains $Na^+$ (or other cations) to charge balance the carboxylate anions of the polymer chain. The term "anionic polymer" is used to describe such a polymer whereas a cationic polymer is one where the polymer chain is cationic with anions, such as fluoride, hydroxide, borate, etc., used to charge balance the polymer chain. Such materials are described in U.S. Pat. No. 3,288,770. The methods of preparing the polyacrylamides are disclosed, for example, in U.S. Pat. No. 2,820,777.

The polyacrylamides described above, even in the anionic form, have a very high molecular weight and are soluble in water, but only to a modest extent. Solutions having a concentration of 0.5 weight percent polymer can be prepared; however, above 0.2 weight percent the viscosity becomes too great for convenient use. The preferred concentrations are in the range of 0.01 to 0.15 weight percent.

It is necessary that an aqueous solution of the polyacrylamide be used, for the undissolved polyacrylamide will have little, if any, effect as a coagulating agent. It is believed that the polyacrylamide functions as a coagulant by stringing out the long molecules of the polyacrylamide in water and literally dragging the alumina particles down to the bottom of the settling vessel. It is surprising that only a small but nonetheless definite amount of the polyacrylamide is required to provide this result. For example, it has been found that amounts as little as 1–2 ppm of the polyacrylamide in the total aqueous suspension of alumina particles are sufficient to result in substantially complete settling of the alumina in very short periods of time, on the order of five to ten minutes. Amounts as low as 0.4 ppm are not suitable. The range of concentration of polyacrylamide can therefore suitably be from 0.5 to 10 ppm but is more usually from 1 to 5 ppm. Larger amounts of the polyacrylamide can be employed, for example, 100 ppm or more, but serve no useful purpose. Because of the variation in molecular weight and amide group conversion, those with ordinary skill in the art can with very little experimentation determine the proper amount of anionic polyacrylamide to use to result in settling of at least 90 weight percent of the alumina in less than 10 minutes at ambient conditions.

The process of this invention may perhaps be more readily understood by reference to the attached FIG. 1.

Referring to FIG. 1, effluent from the alpha-olefin process (a mixture of alpha-olefins having from $C_4$ to $C_{40}$ carbon atoms per molecule, plus the aluminum alkyl catalyst) is charged through line 10 into mixing tank 12 along with water through line 14. Any suitable means of contacting can be employed in the mixing tank 12, which is at a temperature of 75° C. The reaction between the water and the aluminum alkyl is so fast that a mixing valve can suitably be employed instead of a mixing tank if so desired. The alpha-olefin process effluent stream charged through line 10 is under a pressure of about 600 psig and typically contains about 49 percent alpha-olefin product, about 49 percent unreacted ethylene, and about 2 percent of organo-aluminum catalyst. The discharge from the mixer 12 is under a pressure from about 50 to 1000 psig and passes through line 16 to a first aluminum-removal chamber 18, which is at a temperature of 75° C. Gaseous ethylene under a pressure of about 220 psig passes out of chamber 18 overhead through line 19 to a suitable recovery section (not shown). In chamber 18, an organic layer overlies an aqueous layer. The organic layer is removed through line 20 into a second separator 24, and additional amounts of water on the order of 15 to 100 volume percent based on the amount of the organic layer entering through line 20 are added intermittently as needed through line 26 and serve to wash out any remaining small amounts of aluminum which may be present in the organic layer. Again, an organic layer overlies an aqueous layer in separator 24, and the organic layer is removed through line 28 to suitable distillation or other separation schemes (not shown).

The aqueous layer from separator 24 is removed through the bottom of chamber 24 through line 30, and this aqueous layer contains small amounts of colloidal aluminum hydroxide. The aqueous layer from line 30 is admixed with the aqueous layer in line 22 which is then removed from the bottom of chamber 18. The aqueous stream in line 22 enters the second aluminum removal zone 32 at a pressure of about 0 to 15 psig and any suitable temperature. An aqueous solution containing about 0.01 to 0.15 weight percent of a polyacrylamide in anionic form enters the settling chamber 32 through line 34. A sufficient amount of the polyacrylamide is added through line 34 to amount to about 2 parts per million of polyacrylamide in the total medium in settling chamber 32. Settling of a colloidal aluminum hydroxide occurs very rapidly in the settling chamber 32, and a supernatant water layer can be removed from settling chamber 32 near the top through line 36 for recycle to mixer 12 through line 14. A slurry of hydrated alumina is removed from settling chamber 32 through line 38 and is sent to a suitable separation device such as a rotary vacuum filter 40. Water is removed from rotary vacuum filter 40 through line 14, where it is recycled to the mixer 12. The hydrated alumina filtercake is removed from rotary vacuum filter 40 through line 42 where it can be sent to a suitable drying mechanism such as a rotary tube dryer 44. Water is removed from the rotary tube dryer 44 through line 46, and this can also be recycled to the mixer 12 if desired.

The dry form of the hydrated alumina is removed from the rotary tube dryer 44 through line 48. It is noted that the alumina produced by the process of this invention is extremely pure and thus quite suitable for use as a catalytic support alumina for non-cracking catalysts, such as reforming catalysts.

The invention will be further described with reference to the following experimental work.

The alpha-olefin - aluminum alkyl mixture used in the following experiments was obtained from a commercial alpha-olefin plant. The mixture contained the approximate composition as shown in Table I below:

TABLE I

Alpha-Olefin Reactor Effluent

| Carbon No. | Wt % |
|---|---|
| $C_2$ | 40.00 |
| $C_4$ | 7.62 |
| $C_6$ | 8.16 |
| $C_8$ | 7.80 |
| $C_{10}$ | 6.96 |
| $C_{12}$ | 5.94 |
| $C_{14}$ | 4.98 |
| $C_{16}$ | 4.02 |
| $C_{18}$ | 3.24 |
| $C_{20}$ | 2.58 |
| $C_{22}$ | 2.04 |
| $C_{24}$ | 1.56 |
| $C_{26}$ | 1.20 |
| $C_{28}$ | 0.96 |
| $C_{30}^+$ | 2.94 |

The mixture was transported in LPG cylinders without exposure to oxygen or air. It is, of course, well known that it is necessary to avoid contact of the alpha-olefin aluminum alkyl mixture with air or oxygen because the aluminum alkyl in the mixture would react immediately with the oxygen to form an aluminum alkoxide which would result in alcohol formation upon hydrolysis rather than the desired hydrated aluminum oxide.

The LPG cylinder was heated to a temperature of approximately 45° to 50° C. to insure that the alpha-olefin-aluminum alkyl mixture was in a molten state. There are sufficient higher molecular weight alpha-olefin telomers in the mixture that they resemble wax-like materials, and the entire mixture tends to solidify on cooling to room temperature.

The valve on the heated LPG cylinder was opened and the mixture of olefins shown in Table 1 was fed into the bottom of a vessel containing about 19 liters of water and heated to about 70° C. The vessel was mechanically stirred and, in addition, some mixing was achieved by the gaseous olefin portion of the olefin mixture bubbling through the water — olefin mixture. The addition of olefins to the water vessel was continued until the liquid volume in the vessel had about doubled.

The water phase containing the colloidal hydrated aluminum oxide was drained from the bottom of the mixing vessel into a receiver, and the alpha-olefin layer was separately collected.

A series of experiments were performed using various materials to improve the very sluggish settling rate of the hydrated alumina from the aqueous colloidal suspension, resulting from the hydrolysis of the alpha-olefin - organo-aluminum reaction product. In each of the experiments, an aliquot 1000 cc portion of the colloidal hydrated aluminum suspension was admixed with a small concentration of an agent to determine the effect of the agent on the settling rate of the alumina from the suspension. All of the experiments were done at atmospheric pressure and room temperature. The results are summarized in Table II below:

TABLE II

EFFECT OF VARIOUS COAGULANT AIDS ON THE RATE OF SETTLING OF THE HYDRATED ALUMINA

| Ex. No. | Coagulant Aid | Concentration of Coagulant Aid, ppm by wt. | Results |
|---|---|---|---|
| 1 | Anionic polyacrylamide* | 0.4 | Some settling in 5 min. Remaining solids in suspension after 24 hrs. |
| 2 | '' | 1 | About 90% settled in 5 min. |
| 3 | '' | 2 | Greater than 90% (about 100%) settled in 4 min. |
| 4 | '' | 2.5 | 95% settled in 1.5 min.; 99% in 2 minutes |
| 5 | '' | 3.0 | 99% in 1 minute |
| 6 | Nothing | 0 | Some settling in 24 hrs.; considerable material still suspended. |
| 7 | Cationic polyelectrolyte** | 1 | Small amount settled in 24 hrs. |
| 8 | '' | 5 | Small amount settled in 24 hrs. |
| 9 | '' | 10 | Larger amount settled but still settling after 24 hours. |
| 10 | Urea | about 3 grams per 1600 cc of suspension | No settling while standing over weekend, i.e. 48 hours |
| 11 | Oxalic acid | 0.1 gram per 1600 cc of suspension | Milky ppt. formed; would not settle out. |
| 13 | $Al_2(SO_4)_3 \cdot H_2O$ | 50 ppm | No settling in 12 hrs. |
| 14 | '' | 100 ppm | Some settling in 8 hrs. Clear solution in 24 hrs. |

*Obtained from Calgon Corp. as WT-27C0.
**Obtained from Calgon Corp. as Cat-Floc T Referring to Table II above, it can be seen that only the anionic polyacrylamide was successful among a number of known coagulant aids for the efficient settling of the hydrated alumina made by the hydrolysis of the alpha-olefin - organo-aluminum reation product. Thus, again referring to Table II, Examples 1–5 represent the process of this invention and indicate that a small but definite concentration of the anionic polyacrylamide is necessary to result in efficient settling of the hydrated alumina, and that amounts as low as 1 part per million result in greater than 90 percent settling of the hydrated alumina in time periods of about 5 minutes (Ex. 2). As the amount of anionic polyacrylamide is raised to the 2- to 3-part-per-million range, the settling is substantially completed in time periods of 1 to 4 minutes. When no coagulant aid is employed, there is a slow but definite settling of the hydrated alumina over time periods of 24 hours, which accounts in part for the difficulties in wall coating and transfer line fouling realized by prior art workers such as Fernald et al. mentioned above. As is shown in Examples 7 through 14, the addition of other known coagulant aids such as cationic polyelectrolytes, aluminum sulfate, urea, and organic acids, has very little positive effect on improving the settling rate of the particular form of hydrated alumina made by the process of this invention.

The hydrated aluminum oxide flock resulting from the addition of the flocculating agent of this invention is much coarser than the fine particles of the hydrated aluminum oxide precipitate in the absence of the flocculating agent. These coarser particles do not blind the filter paper as the fine particles do, and filtration is much faster (about 2 to 5 times) when the flocculating agent of this invention is used.

The precipitate from Example 3 above was filtered and dried at approximately 120° C. The dried filtercake was analyzed by X-ray diffraction and was found to have a pattern shown on FIG. 2. This X-ray diffraction pattern corresponds to a pseudoboehmite form of alumina hydrate, and water loss measurements indicate the chemical composition to be $Al_2O_3 \cdot 2H_2O$. Usually the alumina hydrate wil have the formula $Al_2O_3$ with 1 to 3 moles of hydrate water per mole of alumina. Such a type of material is known to be a precursor of a useful catalytic alumina. (See U.S. Pat. Nos. 3,188,174 and 3,222,273.)

The dried alumina having the X-ray diffraction pattern shown in FIG. 2 was then calcined in air at a temperature of 500° C. for 16 hours, and the physical characteristics of the calcined alumina are shown in Table III below:

TABLE III

| Pore Characteristics of Calcined Alumina Precipitate from Alpha-Olefin Residue | |
|---|---|
| Pore Vol., cc/g | 0.63 |
| Av. Pore Radius, A | 43.4 |
| BET Surface Area, m²/g | 289.8 |
| PSD, vol % | |
| 200–300   A (radius) | 2.5 |
| 100–200 | 10.4 |
| 50–100 | 31.7 |
| 30–50 | 37.2 |
| 15–30 | 18.2 |
| <15 | 0 |

Referring to Table III, it can be seen that these pore characteristics are quite acceptable for the use of this calcined alumina as a catalyst support for hydrotreating and/or reforming applications. In addition, the material is extremely pure when precipitated using the anionic polyacrylamides defined above, rather than inorganic agents such as aluminum sulfate where the sulfur would introduce undesired impurities even if they were successful in working.

Resort may be had to such variations and modifications as fall within the spirit of the invention and the scope of the appended claims.

We claim:

1. A process for the removal of aluminum from the product stream of an alpha-olefin process wherein ethylene is polymerized to alpha-olefins in the presence of an organo-aluminum catalyst to produce a product stream containing said organo-aluminum catalyst in the alpha-olefins comprising:

mixing water with said product stream in an amount sufficient to produce:
  a. an aqueous phase containing a fine suspension of aluminum hydroxide particles, and
  b. an alpha-olefin phase;
and thereafter adding a sufficient amount of an aqueous solution of a polyacrylamide to said aqueous phase containing said suspension to result in at least 90 weight percent of the aluminum hydroxide in said suspension to settle from said suspension in less than ten minutes at ambient conditions, said polyacrylamide having the formula:

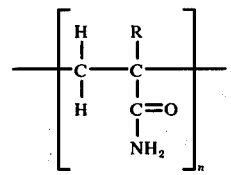

where R can be hydrogen or a hydrocarbon group having from 1 to 6 carbon atoms; n is from $80 \times 10^3$ to $15 \times 10^5$; and wherein a sufficient portion of the $NH_2$ groups are converted to an acid salt form to impart anionic properties to the polyacrylamide.

2. A process for the removal of aluminum from the product stream of an alpha-olefin process wherein ethylene is polymerized to alpha-olefins in the presence of an organo-aluminum catalyst to produce a product stream containing said organo-aluminum catalyst in the alpha-olefins comprising:

mixing water with said product stream in an amount sufficient to produce:
  a. an aqueous phase containing a fine suspension of aluminum hydroxide particles, and
  b. an alpha-olefin phase;
separating said aqueous phase from said alpha-olefin phase;
and thereafter adding a sufficient amount of an aqueous solution of a polyacrylamide to said aqueous phase containing said suspension to result in at least 90 weight percent of the aluminum hydroxide in said suspension to settle from said suspension in less than ten minutes at ambient conditions, said polyacrylamide having the formula:

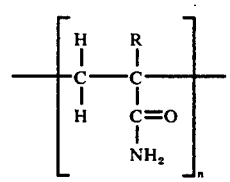

where R can be hydrogen or a hydrocarbon group having from 1 to 6 carbon atoms; n is from $80 \times 10^3$ to $15 \times 10^5$; and wherein a sufficient portion of the $NH_2$ groups are converted to an acid salt form to impart anionic properties to the polyacrylamide.

3. A process for the removal of aluminum from the product stream of an alpha-olefin process wherein ethylene is polymerized to alpha-olefins in the presence of an organo-aluminum catalyst to produce a product stream containing said organo-aluminum catalyst in the alpha-olefins comprising:

mixing water with said product stream in an amount such that the volume ratio of water to said product stream is from 0.25:1 to 2:1 to produce in a first aluminum removal zone:
a. an aqueous phase containing suspension of aluminum hydroxide particles, and
b. an alpha-olefin phase;
removing said aqueous phase to a second aluminum removal zone;
adding a sufficient amount of an aqueous solution of a polyacrylamide to result in at least 90 weight percent of the aluminum hydroxide in said suspension to settle from said suspension in less than ten minutes at ambient conditions, said polyacrylamide having the formula:

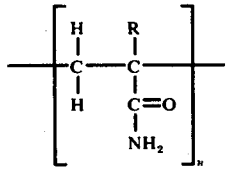

where R can be a hydrogen or a hydrocarbon group having from 1 to 6 carbon atoms; $n$ is from $80 \times 10^3$ to $15 \times 10^5$; and wherein a sufficient portion of the $NH_2$ groups are converted to an acid salt form to impart anionic properties to the polyacrylamide.

4. A process according to claim 3 wherein about 15 percent of the $NH_2$ groups in said polyacrylamide are converted to the acid salt form.

5. A process according to claim 4 wherein the $NH_2$ groups in said polyacrylamide are converted to the acid salt form by reaction with $H_2SO_4$.

6. A process according to claim 5 wherein the volume ratio of water to said product stream in said first removal zone is about 1:1.

7. A process according to claim 4 wherein the $NH_2$ groups in said polyacrylamide are hydrolyzed by treatment with an aqueous solution of an alkali metal hydroxide.

8. A process according to claim 7 wherein the volume ratio of water to said product stream in said first removal zone is about 1:1.

* * * * *